(12) United States Patent
Otto et al.

(10) Patent No.: US 7,734,010 B2
(45) Date of Patent: Jun. 8, 2010

(54) METHOD AND APPARATUS FOR PLANNING AND DELIVERING RADIATION TREATMENT

(75) Inventors: Karl Otto, Vancouver (CA); Marie-Pierre Milette, Vancouver (CA)

(73) Assignee: BC Cancer Agency, Vancouver (CA)

( * ) Notice: Subject to any disclaimer, the term of this patent is extended or adjusted under 35 U.S.C. 154(b) by 486 days.

(21) Appl. No.: 11/383,188

(22) Filed: May 12, 2006

(65) Prior Publication Data

US 2006/0256915 A1  Nov. 16, 2006

Related U.S. Application Data

(60) Provisional application No. 60/680,507, filed on May 13, 2005.

(51) Int. Cl.
 *A61N 5/10* (2006.01)
(52) U.S. Cl. ............... 378/65; 378/147; 378/150; 378/151; 378/152; 378/153
(58) Field of Classification Search ........... 378/65, 378/147–153
See application file for complete search history.

(56) References Cited

U.S. PATENT DOCUMENTS

| | | | |
|---|---|---|---|
| 4,868,843 A | 9/1989 | Nunan | |
| 4,868,844 A | 9/1989 | Nunan | |
| 5,332,908 A | 7/1994 | Weidlich | |
| 5,591,983 A | 1/1997 | Yao | |
| 5,663,999 A | 9/1997 | Siochi | |
| 5,748,703 A | 5/1998 | Cosman | |
| 5,757,881 A | 5/1998 | Hughes | |
| 5,802,136 A | 9/1998 | Carol | |
| 5,818,902 A | 10/1998 | Yu | |
| 6,038,283 A | 3/2000 | Carol et al. | |
| 6,052,430 A | 4/2000 | Siochi et al. | |
| 6,108,400 A | 8/2000 | Siochi | |
| 6,134,296 A | 10/2000 | Siochi | |
| 6,142,925 A | 11/2000 | Siochi et al. | |
| 6,240,161 B1 | 5/2001 | Siochi | |
| 6,260,005 B1 | 7/2001 | Yang et al. | |
| 6,278,766 B1 | 8/2001 | Kooy et al. | |
| 6,314,159 B1 | 11/2001 | Siochi | |

(Continued)

FOREIGN PATENT DOCUMENTS

WO  99/48558 A1  9/1999

(Continued)

OTHER PUBLICATIONS

Enhancement of IMRT delivery through MLC rotation, Phys. Med. Biol. 47, 3997-4017, 2002.*

*Primary Examiner*—Hoon Song
*Assistant Examiner*—Mona M Sanei
(74) *Attorney, Agent, or Firm*—Oyen Wiggs Green & Mutala LLP

(57) ABSTRACT

Radiation may be delivered in a number of segments shaped by a multi-leaf collimator. The collimator may be at different angles of rotation for the different segments. A method for planning radiation treatment involves obtaining an optimized set of collimator configurations by a direct aperture optimization method that takes into account collimator rotation. In some embodiments, area constraints are applied to the optimization. Methods according to embodiments of the invention can generate efficient treatment plans.

39 Claims, 12 Drawing Sheets

U.S. PATENT DOCUMENTS

| | | |
|---|---|---|
| 6,330,300 B1 | 12/2001 | Siochi |
| 6,335,961 B1 | 1/2002 | Wofford et al. |
| 6,349,129 B1 | 2/2002 | Siochi |
| 6,393,096 B1 | 5/2002 | Carol et al. |
| 6,473,490 B1 | 10/2002 | Siochi |
| 6,504,899 B2 | 1/2003 | Pugachev et al. |
| 6,560,311 B1 | 5/2003 | Shepard et al. |
| 6,757,355 B1 | 6/2004 | Siochi |
| 7,162,008 B2 * | 1/2007 | Earl et al. .................... 378/65 |
| 2002/0006182 A1 | 1/2002 | Kim et al. |
| 2003/0086530 A1 * | 5/2003 | Otto ........................... 378/65 |
| 2004/0071261 A1 * | 4/2004 | Earl et al. .................... 378/65 |

FOREIGN PATENT DOCUMENTS

| | | |
|---|---|---|
| WO | 00/15299 A1 | 3/2000 |
| WO | 01/60236 A2 | 8/2001 |
| WO | 02/24277 A1 | 3/2002 |

* cited by examiner

METHOD AND APPARATUS FOR PLANNING AND DELIVERING RADIATION TREATMENT

CROSS-REFERENCE TO RELATED APPLICATION

This application claims the benefit under 35 U.S.C. §119 of U.S. patent application No. 60/680,507 filed on 13 May 2005, which is hereby incorporated herein by reference.

TECHNICAL FIELD

The invention relates to planning and delivering radiation treatments. The invention encompasses methods, apparatus and computer program products. Specific embodiments provide methods and apparatus for establishing apertures for delivering desired radiation dose distributions. The invention may be applied to the determination of apertures to be used in intensity modulated radiation therapy (IMRT).

BACKGROUND

Various medical conditions can be treated by way of radiation therapy. For example, some cancers can be treated by exposure to radiation. Modern methods attempt to deliver radiation dose distributions which are designed carefully to deliver radiation to desired locations while sparing surrounding tissues in a subject. Intensity modulated radiation therapy (IMRT) is one such method.

Radiation delivery apparatus can have a large number of degrees of freedom. Typical radiation delivery apparatus has a source of radiation, such as a linear accelerator and a rotatable gantry. The gantry can be rotated to cause radiation to be incident on a subject from different angles. The shape of the incident radiation beam can be modified by a multi-leaf collimator. The multi-leaf collimator has a number of leaves that are substantially opaque to radiation. The leaves can be advanced to block radiation in a portion of the beam or retracted to allow radiation to pass. The multi-leaf collimator may be rotated to different angles. Some modes of delivering radiation that make use of a rotatable multi-leaf collimator are described in Otto, U.S. Pat. No. 6,907,105, which is hereby incorporated by reference herein.

A radiation treatment plan for a subject typically specifies a three-dimensional distribution of radiation dose that it is desired to deliver to a target region within the subject. The desired dose distribution typically specifies dose values for voxels lying within the target. Ideally, no radiation would be delivered to tissues outside of the target. The goal in Intensity Modulated Radiation Therapy (IMRT) inverse planning is to generate a desired dose in the target while reducing the dose as much as possible to critical structures and healthy tissue.

After a desired dose distribution has been established, treatment planning is conventionally performed in two steps. First, fluence maps for a number of predetermined gantry angles are updated iteratively under the constraints of a cost function until a set of fluence maps that yields an optimal dose distribution is obtained. Second, field shapes that will generate the optimal fluence maps are generated using a leaf sequencing algorithm. Constraints imposed by the structure of a multi-leaf collimator (MLC) to be used in shaping the radiation are taken into account during the leaf sequencing step. Various aspects of this conventional approach to treatment planning are given in:

S. V. Spirou and C. S. Chui. *A gradient inverse planning algorithm with dose-volume constraints*, Med. Phys. 25, 321-333 (1998);

Q. Wu and R. Mohand. *Algorithm and functionality of an intensity modulated radiotherapy optimization system*, Med. Phys. 27, 701-711 (2000);

S. V. Spirou and C. S. Chui. *Generation of arbitrary intensity profiles by dynamic jaws or multileaf collimators*, Med. Phys. 21, 1031-1041 (1994);

P. Xia and L. J. Verhey. *Multileaf collimator leaf sequencing algorithm for intensity modulated beams with multiple static segments*, Med. Phys. 25, 1424-1434 (1998); and K. Otto and B. G. Clark. *Enhancement of IMRT delivery through MLC rotation,"* Phys. Med. Biol. 47, 3997-4017 (2002).

The degrees of freedom available in typical radiation treatment apparatus mean that, a given desired dose distribution can typically be achieved by applying any of a wide range of possible sequences of fields. There is a need for ways to identify an optimum, or nearly optimum, set of fields.

SUMMARY OF THE INVENTION

The invention relates to methods and apparatus for deriving collimated apertures and collimator angles for allowing a radiation delivery apparatus to be controlled to deliver a desired radiation dose. The methods may be called generally Rotating Aperture Optimization (RAO) methods.

One aspect of the invention provides a method for use in radiation treatment. The method comprises modifying a set of variables to reduce a cost function. The set of variables defines apertures for a plurality of segments including at least first and second segments respectively corresponding to different first and second angles of rotation of a collimator about a beam direction. The method also comprises computing the cost function based at least in part upon a volume dose distribution computed for the set of variables.

Another aspect of the invention provides a method for use in radiation treatment of a target in a subject, the method comprises: providing a prescribed volume dose distribution; initializing a set of variables, the set of variables including, collimator configurations for a plurality of segments, the segments corresponding to a plurality of angles of rotation of a rotatable multi-leaf collimator and a plurality of beams, each of the collimator configurations specifying positions of leaves of the collimator; determining a computed volume dose distribution for the set of variables; computing a cost function based at least in part on differences between the computed volume dose distribution and the prescribed volume dose distribution and making the cost function a current cost function; and, optimizing the set of variables. Optimizing the set of variables comprises, until a termination condition is satisfied: changing one or more variables of the set of variables to yield a changed set of variables; computing an updated cost function for the changed set of variables; and, based at least in part upon a comparison of the updated cost function to the current cost function, determining whether or not to make the changed set of variables the current set of variables and the updated cost function the current cost function.

Another aspect of the invention provides radiation treatment apparatus comprising: dose computation means for computing a volume dose distribution corresponding to a set of variables defining apertures for a plurality of segments including at least first and second segments respectively corresponding to different first and second angles of rotation of a collimator about a beam direction; means for evaluating a value of a cost function based at least in part upon a volume dose distribution from the dose computation means; and, means for modifying the set of variables to reduce the value of the cost function.

Further aspects of the invention and features of specific embodiments of the invention are described below.

BRIEF DESCRIPTION OF THE DRAWINGS

In drawings which illustrate non-limiting embodiments of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Radiation delivered from a particular gantry angle may be called a "beam". A typical IMRT treatment involves irradiating a subject, in sequence, with each of a plurality of different beams. The dose delivered to tissues surrounding a target, such as a tumor or other lesion, can be minimized by irradiating the target from multiple angles. A map of the fluence delivered by each beam may be called a field. A field may be delivered in one shot or as a succession of a number of sub-fields (either of which may be called a "segment"). Each segment has a shape, which may be called an aperture. The shape may be determined, for example, by a set of positions of leaves of a multi-leaf collimator and an angle of the multi-leaf collimator.

One aspect of this invention provides methods for planning the delivery of radiation so that a dose distribution that closely matches a desired dose distribution can be delivered to a subject. The method exploits collimator rotation. A direct aperture optimization (DAO) algorithm is used to identify an optimum set of fields for delivering a specified dose distribution. As described below, the DAO algorithm may incorporate a simulated annealing algorithm. In alternative embodiments, other direct aperture optimization methods are used. Such alternative DAO methods include but are not limited to:

- algorithms in which MLC leaf positions and the segment weights are adjusted iteratively;
- simulated annealing techniques; and,
- genetic algorithms.

Figure 1:
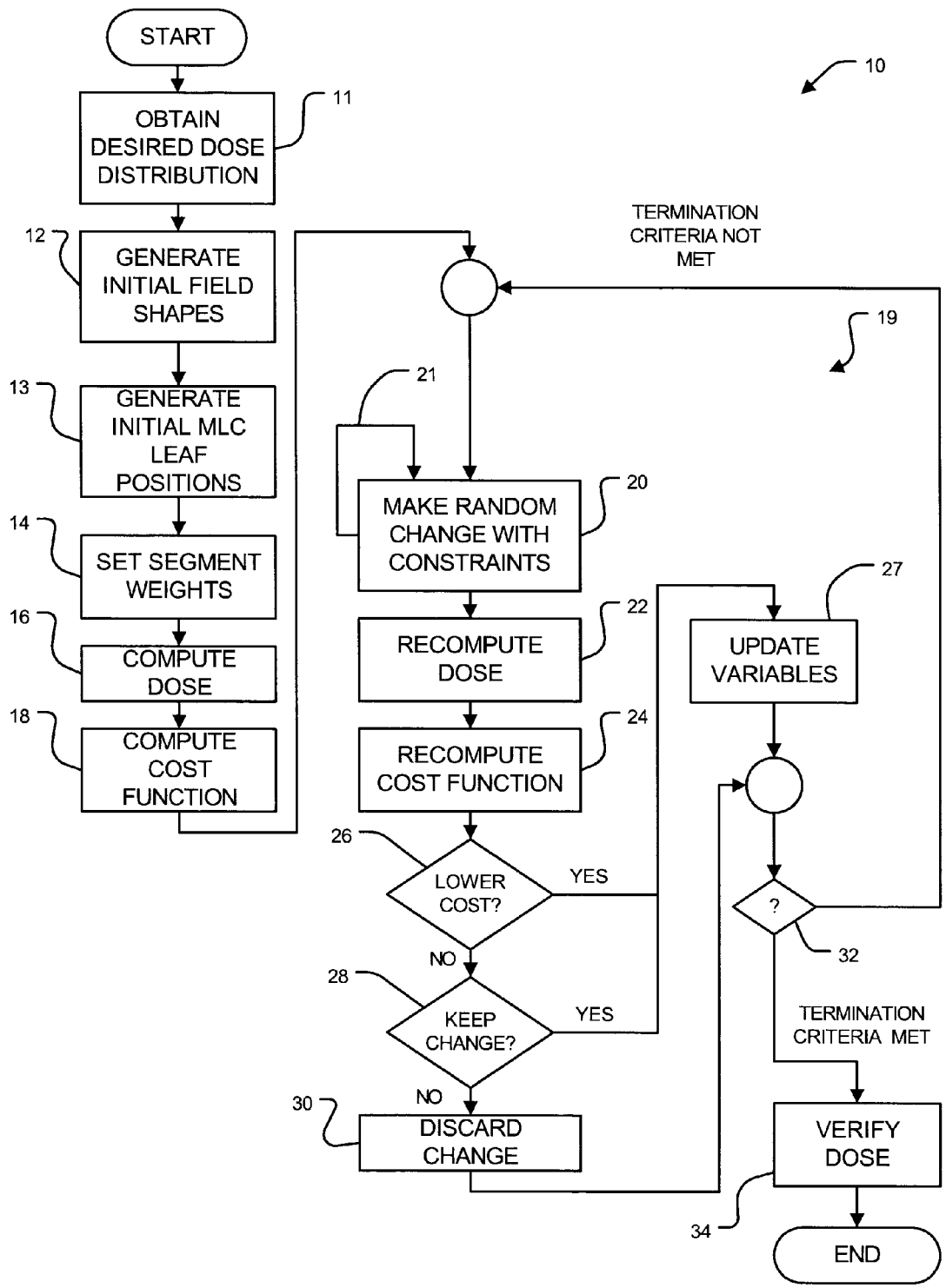
FIG. 1 is a flow chart which illustrates a method for determining apertures to be used in intensity modulated radiation therapy according to one embodiment of the invention.

FIG. 1 illustrates a fluence-based optimization method 10 according to an embodiment of the invention. Method 10 may be performed in a programmed data processor, for example. Method 10 begins in block 11 with obtaining a desired radiation dose distribution. Block 11 may comprise accessing data specifying the desired dose distribution which may have been developed previously using any suitable techniques. Block 12 generates an initial set of field shapes. The field shapes are generated for each of a plurality of beams. The field shapes may be set to be, or to approximate, the beam's-eye-view of the target for each beam.

In block 13, an initial set of leaf positions is generated for each of a plurality of segments. The initial leaf positions may be set to approximate the initial field shape for the beam to which the segment belongs. This is not necessary, however. Other initial leaf positions could be used. For example, one could set all leaves to be closed initially.

The segments preferably include at least segments for a plurality of different collimator angles for each of one or more beams. The different collimator angles may be separated by fixed angular steps. The collimator could be rotated in steps of a few degrees or more between the segments. For example, the collimator could be rotated by steps in the range of 1 to 60 degrees between the segments. Note that the collimator is typically symmetrical with respect to inversions and so any collimator rotation angle can typically be mapped into a collimator angle in the range of 0 degrees to 180 degrees, where 0 degrees is an arbitrary reference angle. The segments may have collimator rotations that are distributed uniformly over the range of 0 to 180 degrees. For example, if there are nine segments for each beam then the segments could be separated by steps of 18 degrees in collimator rotation. It is convenient but not mandatory that the segments be at equally spaced-apart collimator angles. It is convenient, but not mandatory, to provide the same number of segments for each beam.

Typically there are three or more beams. In many cases, 5 or more beams may be used.

In block 14 weights are set for each segment. The weights may initially all be set to be equal to one another.

In block 16 a computed dose distribution is computed. Computation of the dose may be performed by summing together a contribution to the dose from each of the segments. The computation may comprise treating each segment as being made up of a plurality of pencil beams of radiation that are allowed to pass by the multileaf collimator and then summing the contributions from the pencil radiation beams.

The pencil beams may be called "beamlets" and may have any convenient shapes and sizes. The pencil beams may be defined by a fluence grid that divides a beam into an array of pencil beams. The array may be a regular array such as a rectilinear array. For example, FIG. 1C is a schematic cross-sectional view of an example fluence grid 100 that divides an arbitrary portion of a beam 102 into an array of pencil beams 104.

Since the segments are generated with a multi-leaf collimator at different angles of rotation, it is desirable to make dose computations using pencil beams that are smaller than the width of the leaves of the multi-leaf collimator. In some embodiments, a fluence pixel size of 2.5 mm by 2.5 mm is used. The positions of the leaves in the multi-leaf collimator determine which of the pencil beams can contribute to the delivered dose. A group of contributing pencil beams may be determined in advance for every possible position of each leaf for each collimator angle. Given a collimator angle and a set of leaf positions the pencil beams that can contribute to the segment dose can be looked up from a stored table in computer memory.

Typically, especially for collimator angles that are not aligned with the fluence grid used to divide a beam into pencil beams, some pencil beams will be partially obstructed by leaves of the multi-leaf collimator. The effect of each of these partially obstructed pencil beams on the calculated dose can be scaled in proportion to the area of the pencil beam that is unobstructed relative to the total area of the pencil beam. These proportions are determined by the geometry of the multi-leaf collimator and may be determined in advance and stored for lookup. By using the fractional area of fluence pixels it is only necessary to maintain one grid of pencil beam doses per beam direction. This reduces computation requirements.

In general, a collimator is not completely opaque to radiation. For example, a collimator in a linear accelerator used by the inventors transmits approximately 1.6% of the radiation that is obstructed by the collimator. The radiation transmitted through leaves of the collimator ought to be taken into account in computing the contribution to the volume dose distribution for a segment.

Any suitable method for computing the dose that would be delivered to voxels in the treatment volume may be used. For example, alternative dose computations, such as Monte-Carlo dose calculations may be used in the alternative. Dose calculation software that may be used to compute the dose is commercially available. One example of commercially-available dose calculation software is the Eclipse™ treatment planning system available from Varian Medical Systems, Inc. of Palo Alto, Calif., USA. The method used to compute the dose should take into consideration the transmission and scatter characteristics of the multi-leaf collimator that will be used to shape the radiation.

In block 18 a cost function is computed. The cost function may be based at least in part upon the dose determined in block 16. In some embodiments, the cost function may, for example, have the general form:

$$f_t = \frac{w_t}{N_t}\left[\sum_{i=1}^{N_t}(D_i - D_{presc}(i))^2\right] \quad (1)$$

where $w_t$ is the priority of the constraint, $N_t$ is the number of voxels in the subject over which the cost function is calculated, $D_i$ is the dose at the $i^{th}$ evaluation point, and $D_{presc}(i)$ is the prescribed dose for the $i^{th}$ evaluation point (in cases where the same dose is specified for the entire target area, $D_{presc}(i)$ will be a constant). The cost function may be computed over all voxels within a target (as well as voxels in surrounding tissues) or, to reduce computation, may be computed over a reduced set of voxels. The voxels in the reduced set may, for example, be quasi-randomly distributed throughout the target and have a density sufficient to obtain accurate results.

It can be seen that the cost function of Equation (1) is minimized for cases where the dose that would be delivered matches the prescribed dose at all evaluation voxels. Alternative cost functions may also be used.

In some embodiments, the cost function also takes into account desired minimum and/or maximum doses delivered to the target. The cost function can be made to take into account a desired minimum dose by adding to the cost function a value that is minimized when all points in the target receive at least the minimum dose. This can be done, for example, by adding to the cost function:

$$\frac{w_t^{min}}{N_t}\sum_{i=1}^{N_t}(D_i - D_{min})^2 H(D_{min} - D_i) \quad (2)$$

where $w_t^{min}$ is a weighting factor, H(x) is the step function having a value of 1 for $x \leq 0$ and having a value of 0 otherwise, and $D_{min}$ is the desired minimum dose.

The cost function can be made to take into account a desired maximum dose by adding to the cost function a value that is minimized when all points in the target receive a dose not exceeding the maximum dose. This can be done, for example, by adding to the cost function:

$$\frac{w_t^{max}}{N_t}\sum_{i=1}^{N_t}(D_i - D_{max})^2 H(D_i - D_{max}) \quad (3)$$

Figure 2:
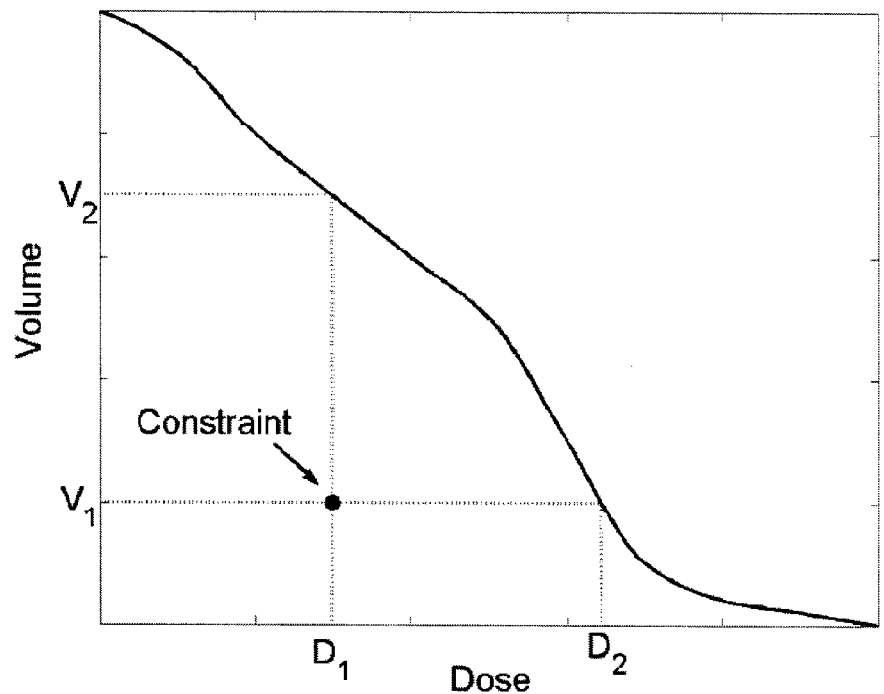
FIG. 2 is an example dose volume histogram marked to illustrate a dose-volume constraint.

The cost function may be made more flexible by taking into account dose-volume constraints. A dose-volume constraint adds cost if the volume receiving a dose greater than some value, $D_1$ exceeds a volume $V_1$. This constraint may be included in a cost function by adding to the cost function the value:

$$f_{OAR} = \frac{w_{OAR}}{N_{OAR}}\sum_{i=1}^{N_t}(D_i - D_1)^2 H(D_i - D_1)H(D_2 - D_1) \quad (4)$$

where $W_{OAR}$ is a weight, $N_{OAR}$ are the number of voxels receiving a dose in the range of $D_1$ to $D_2$ and $D_2$ is a dose such that $V(D_2)=V_1$ in the dose-volume histogram for the voxels used to compute the cost function. Multiple dose-volume constraints may be included in the cost function. FIG. 2 is an example dose-volume histogram that illustrates the selection of $D_2$. The use of dose-volume constraints in other contexts is described in T. Bortfeld, J. Stein, and K. Preiser. *Clinically relevant intensity modulation optimization using physical criteria*. In Proceedings of the XII International Conference on the Use of Computers in Radiation Therapy, Salt Lake City, Utah, pages 1-4, 1997 which is hereby incorporated herein by reference.

It is desirable that the cost function also take into account the area of the aperture provided by each segment. Delivering a treatment through larger apertures tends to reduce the number of monitor units that must be generated to deliver the desired treatment. This can be achieved by including in the cost function a value that decreases if the area of individual apertures is kept above a minimum area or by setting a minimum area as a constraint during optimization (described below). The minimum area is typically set to have a value that is 40% or more of the beam's-eye-view area of the target (i.e. the projected area of the target in the direction of the beam) for the beam in question. It has been found that solutions that provide significant decreases in the number of monitor units required without significantly increasing the cost function can be achieved in the context described herein by setting a constraint requiring that the minimum aperture area be at least approximately 60%, preferably at least approximately 70%. Of the beam's-eye-view area of the target for the beam in question. With constraints of this type, the actual minimum aperture is patient-dependent.

In optimization loop 19 the initial leaf positions and segment weights are iteratively optimized to yield a treatment sequence. In a typical case there are several hundred variables. Consider, for example, the case where there are 5 beams and 6 segments per beam defined by a multi-leaf collimator that has 40 leaves (20 leaf pairs). In this case there will be 5×6×40=1200 leaf positions and 5×6=30 weights for a total of 1230 variables. In block 20 a change is made to one (or more) of the variables to yield a changed set of variables. On the first iteration of optimization loop 19 the current set of variables is the initial set of variables established in blocks 13 and 14. The changes may be made to affect different ones of the variables in a predetermined or random way. For example, in block 20, a random or pseudo-random change may be made to a leaf position or a segment weight of the current set of variables. The particular variable selected may be determined at random. In some embodiments, method 10 cycles through the variables and tries changes to each of the variables in turn.

The change of block 20 is made subject to constraints. The constraints may include, for example Constraints that prohibit impossible collimator leaf configurations—these constraints will depend upon the construction and capabilities of the collimator being used. For example, in some collimators interdigitation of opposing leaves is not possible. The extent of protrusion into the field area of individual leaves is limited in some collimators;

Constraints that limit the aperture so that it does not exceed a beam's eye view of the target; and/or Constraints that require the aperture to be larger than a minimum size. The minimum size may be set as a proportion of the total projected area of the target from the direction of the beam.

Constraints that set a minimum number of monitor units to be delivered for each beam.

Changes that would result in leaf configurations that do not satisfy one or more of the constraints may be rejected automatically. Changes that would result in a negative weight for any segment may be rejected automatically. The automatic rejection of changes that fail to satisfy applied constraints is indicated by line 21.

In some embodiments, the magnitude of the changes may be controlled such that the maximum change decreases over time. For example, the maximum change may be given by:

$$W(n_{succ}) = \frac{W_0}{(1+n_{succ})^{\frac{1}{R}}} \tag{5}$$

where R defines a rate at which the maximum change decreases, $W_0$ is the initial maximum amount of change, and $n_{succ}$ is a value that increases with time. Where a variable being changed is a leaf position then $W_0$ is the initial maximum step size. Where the variable being changed is a weight for a segment then $W_0$ is the initial maximum weight change.

In block 22 the dose is computed for the changed set of variables. In block 24 the cost function is recomputed for the changed set of variables. Blocks 22 and 24 may operate in the same manner as blocks 16 and 18 respectively.

If block 26 determines that the changed set of variables has resulted in a reduction of the cost as compared to the current set of variables then the changed set of variables is made the current set of variables in block 27.

If block 26 determines that the changed set of variables has not resulted in a reduction of the cost as compared to the current set of variables then, in optional block 28 a determination is made as to whether to retain the changed set of variables in any event. If so, then the method proceeds to block 27 where the changed set of variables is made the current set of variables. Otherwise the changed set of variables is rejected in block 30.

Block 28 may involve accepting some changes that result in increases of the cost function with a probability that decreases as the magnitude of the change in the cost function increases. In some embodiments, the probability of keeping the change is proportional to the Metropolis condition given by:

$$P = \exp\left(\frac{-\Delta f}{T}\right) \tag{6}$$

where $\Delta f$ is the change (increase) in the cost function and T is a temperature parameter that decreases over time. In some embodiments, T is given by:

$$T(n_{succ}) = \frac{T_0}{(1+n_{succ})^{\frac{1}{R_T}}} \tag{7}$$

where $T_0$ is an initial "temperature", $R_T$ is a constant which defines a rate of cooling, and $n_{succ}$ is defined above. $n_{succ}$ may be set to be the number of changes to the variables that have been accepted in the iterations of loop 19.

In block 32 the current set of variables is checked to determine whether termination criteria are satisfied. If the termination criteria are not satisfied then method 10 returns to block 20 to repeat loop 19. If the termination criteria are met then the dose resulting from the current set of variables (now a final set of variables) is verified at block 34 and method 10 ends. Any suitable termination criteria may be used. The termination criteria may include criteria such as:

there has been no improvement to the cost function for more than a threshold number of iterations of loop 19;

the cost function for the current set of variables has less than a threshold value;

a certain number of iterations of loop 19 have been made; etc.

It can be appreciated that method 10 offers a number of advantages including:

Physical constraints imposed by the multi-leaf collimator can be built into the optimization and so the method only produces variables that correspond to possible configurations of the multi-leaf collimator.

Method 10 produces radiation delivery sequences that incorporate rotation of a multi-leaf collimator and thus can provide higher spatial resolution, reduced inter-leaf systematic error and increased flexibility in aperture shapes as compared to some prior techniques.

As described below, method 10 can produce treatment plans that are more efficient than treatment plans produced by some prior methods. Improved efficiency can result in a decrease in systematic errors that can result from interleaf leakage and tongue and groove effects.

Radiation that leaks between leaves of the multi-leaf collimator may be compensated for by blocking areas which receive the leakage radiation in other segments. This can be performed automatically by including a model of the radiation leakage in the dose calculations.

To the extent that method 10 produces a treatment plan that is more efficient than a treatment plan that may be obtained in another manner, method 10 contributes to a reduction in the whole-body scatter dose received by a subject. Moreover, treatment times can be reduced;

To the extent that method 10 can produce satisfactory treatment plans that use fewer segments than may be required by other treatment planning methods, method 10 reduces wear and tear on equipment, such as gantry mechanisms and multi-leaf collimators.

While method 10 illustrates potential advantages of an embodiment of the invention, it will be appreciated that some embodiments of the invention do not require that the above advantages be achieved.

Method 10 as set out above, may be described as a direct aperture optimization method that uses a simulated annealing algorithm to select among changed sets of variables. A more detailed description of simulated annealing is provided in S. Kirkpatrick, Jr C. D. Gelatt, and M. P. Vecchi. *Optimization by simulated annealing*, Science 19 220, 671-680 (1983) which is hereby incorporated herein by reference. Other methods for selecting among changed sets of variables may also be used. Such alternative methods include:

purely iterative approaches to adjusting the variables; and
genetic algorithms;

for example.

After method 10 has been performed, a radiation delivery machine, such as a linear accelerator, can be programmed to deliver radiation to a subject according to the final set of variables. The radiation delivery machine sets gantry and collimator rotation angles for each of the sub-beams and sets leaf positions of the multi-leaf collimator for each of the sub beams according to the final set of variables. For each segment the radiation delivery machine delivers an amount of radiation proportional to the weight for the segment as specified in the final set of variables.

Figure 1A:
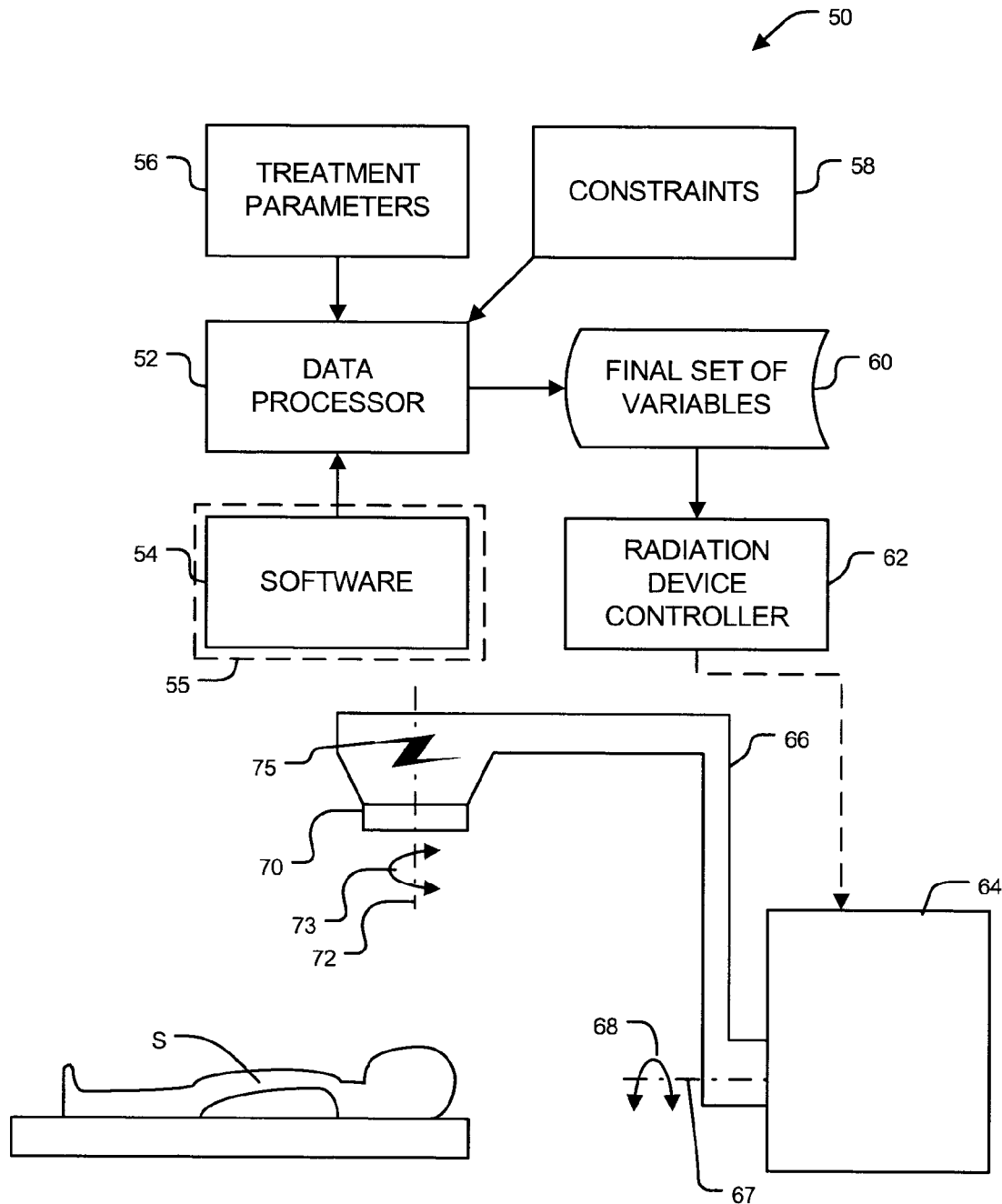
FIG. 1A is a block diagram of apparatus according to an embodiment of the invention.

FIG. 1A shows apparatus 50 according to an embodiment of the invention. Apparatus 50 includes a data processor 52. Data processor 52 may be a data processor in a computer workstation or other computer used as a treatment planning system. Data processor 52 executes computer software 54 that is stored in a memory 55 that data processor 52 can access to execute software 54.

Data processor 52 receives treatment parameters 56 and constraints 58. Treatment parameters 56 may comprise, for example:

data specifying a target and a desired dose distribution within the target;
a number of beams to use and their angles of incidence on the target;
a number of segments to be used for each beam and the collimator rotation angle for each segment;
a beam energy to use in dose calculations;
and so on.

Constraints 58 may include information specifying any of the constraints described above.

Data processor 52 generates a final set of treatment variables 60. Variables 60 are input to a controller 62 for a radiation treatment device 64. Device 64 has a gantry 66 that can be rotated to selected angles about an axis 67 as indicated by arrow 68 under the control of controller 62.

Gantry 66 carries a rotatable multi-leaf collimator 70 that can be rotated about an axis 72 as indicated by arrow 73. Typically axes 72 and 67 are orthogonal to one another and intersect with one another although this is not mandatory. Radiation treatment device 64 includes a source of radiation, such as a linear accelerator, that is indicated schematically by 75.

Controller 62 can cause gantry 66 to move to a desired angle, collimator 70 to rotate to a desired angle, and can set the leaves of collimator 70 to desired positions. Then controller 62 can cause radiation to be emitted from radiation source 75 to irradiate a subject S.

Figure 1B:
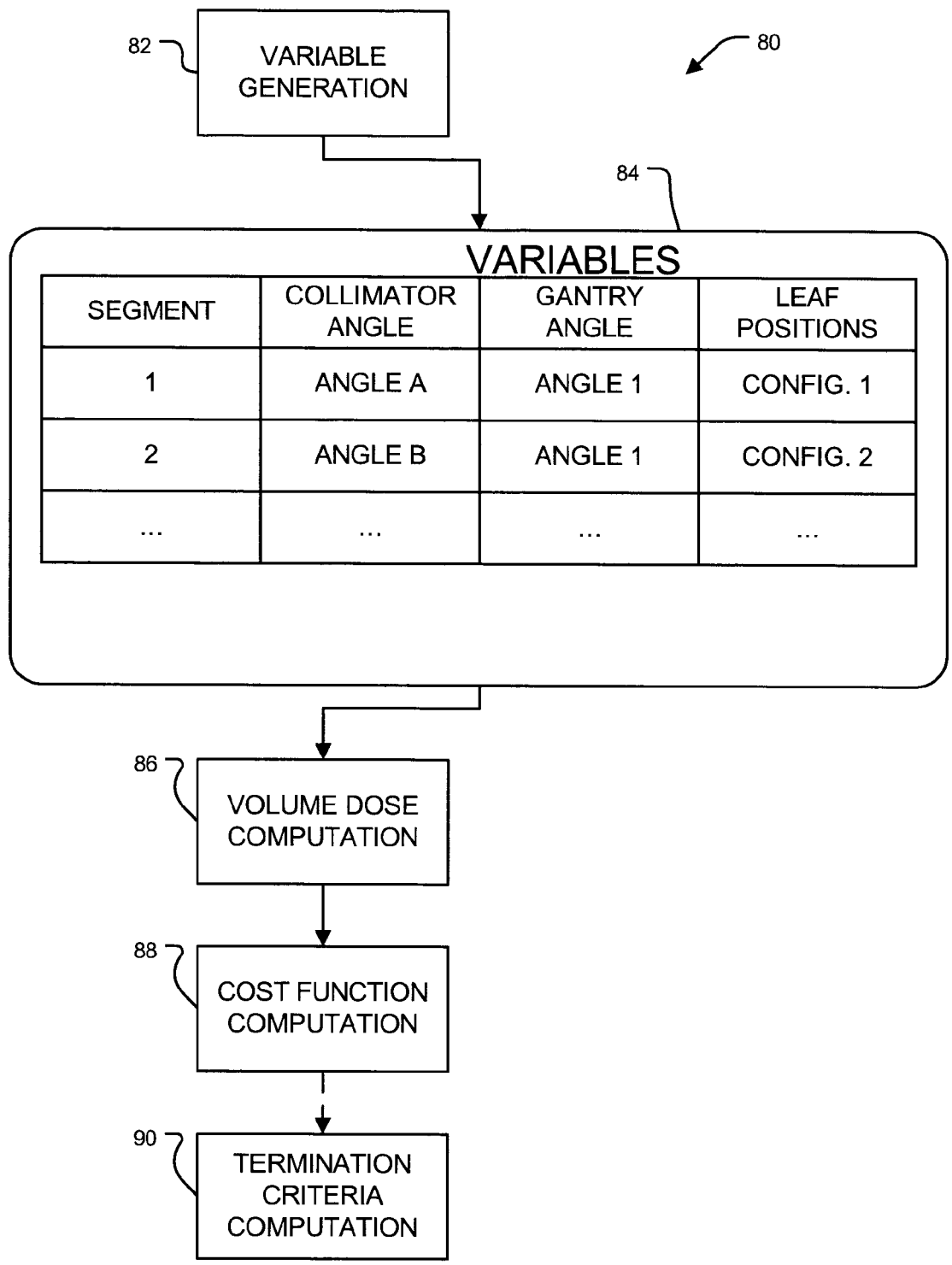
FIG. 1B is a block diagram illustrating functional modules in a processing component.
Figure 1C:
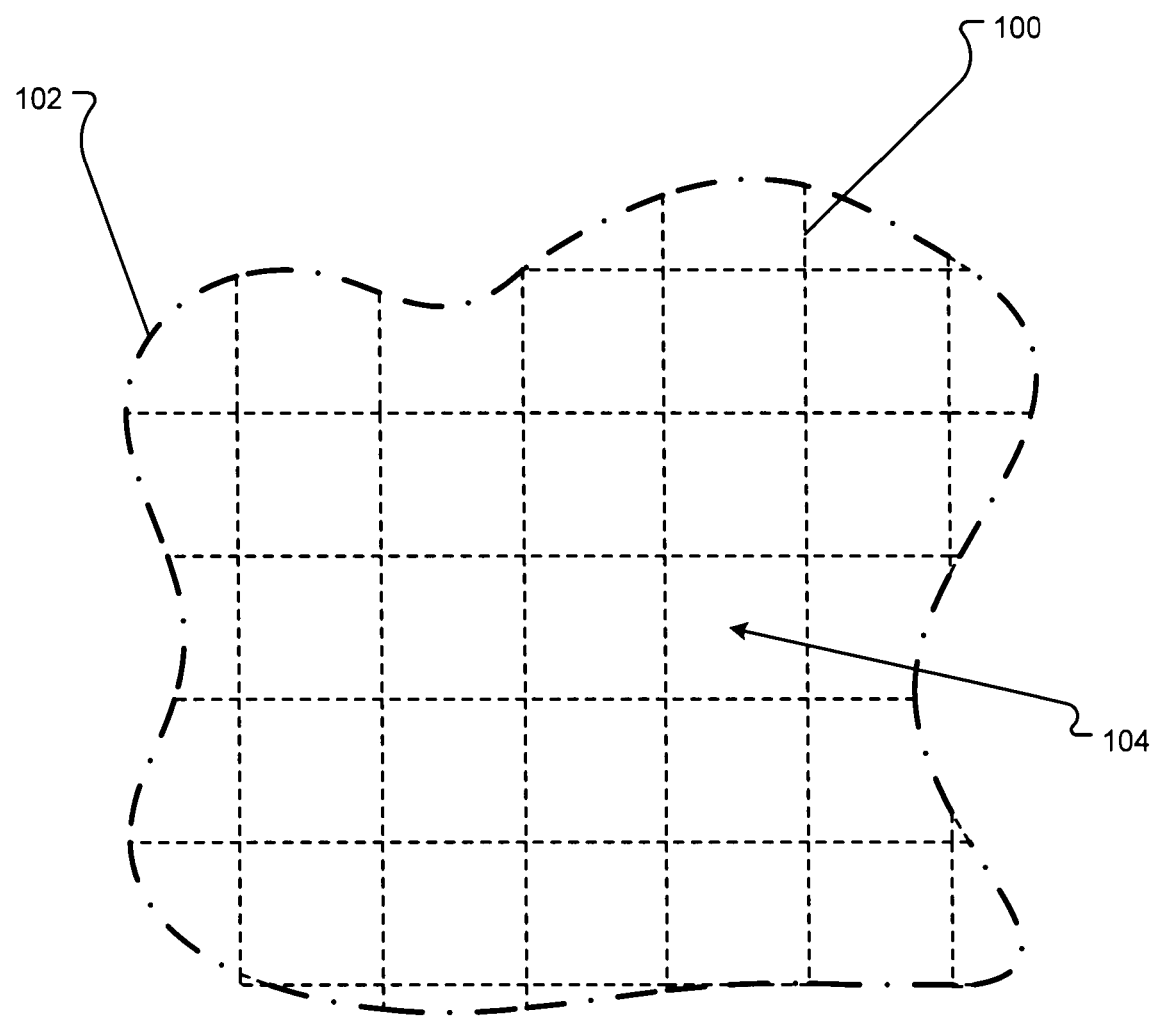
FIG. 1C is a schematic cross-sectional view of an example fluence grid.

FIG. 1B shows functional elements of a data processing apparatus 80 configured according to an example non-limiting embodiment of the invention. The functional elements may be provided by software 54 executing on data processor 52 (FIG. 1A). Apparatus 80 comprises a variable generation module 82 that generates sets 84 of variables. Variable generation module 82 may operate by varying one or more variables of a current set 84.

A dose computation module 86 computes a volume dose distribution that would result from applying set 84 of variables to control a radiation delivery device. Module 86 takes into account collimator angle and can compute volume dose distributions for cases in which the volume dose distribution is contributed to by segments shaped by a collimator that is at different collimator angles for different ones of the segments.

A cost function computation module 88 computes a value of a cost function based at least in part on a volume dose distribution output by module 86. Module 88 may base the value of the cost function in whole or in part on a comparison of the volume dose distribution with a prescribed volume dose distribution. A termination criteria computation module 90 determines when to terminate a process of generating a set of variables for a treatment plan. Module 90 may receive a cost function value from module 88 and/or other inputs.

A prototype embodiment of the method has been performed. Optimization was performed in the MATLAB™ computing environment using pencil beam dose distributions imported from CADPLAN™ treatment planning system version 6.27 available from Varian Medical Systems, Inc. of Palo Alto, Calif., USA. The MATLAB™ computing environment is available from The Mathworks, Inc. of Natick, Mass., United States.

EXAMPLE I

In a first example application, a treatment plan was developed for a prostate patient. Five equi-spaced beams were used. The prescribed dose to the target was set to 74 Gy. Dose limiting constraints were applied to rectum and bladder. The beam energy was 6 MV. A pencil beam (beamlet) size of 2.5 mm by 2.5 mm was used for dose calculations. The voxel size was 2.5 mm by 2.5 mm by 3 mm.

Figure 3:
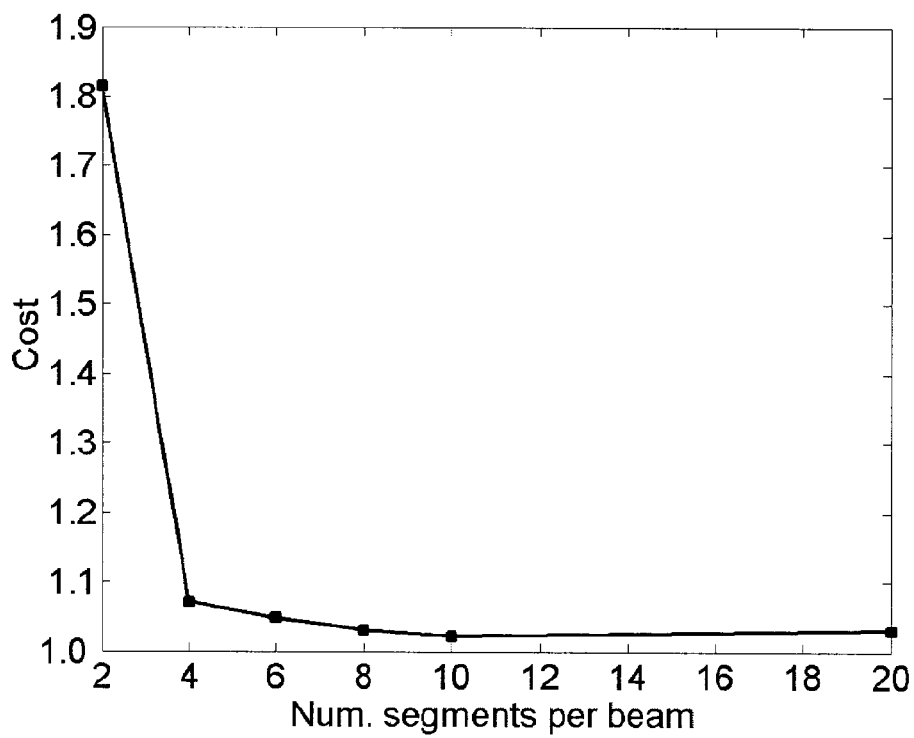
FIG. 3 is a plot showing the value of a cost function as a function of a number of segments for each beam in a treatment plan.

Experiments were done to determine the effect of varying the number of segments per beam. The optimization was run with 2, 4, 6, 8, 10 and 20 rotated segments per field. FIG. 3 shows how the cost function varies with the number of segments per beam. The cost function decreases as the number of segments increases. There is an obvious improvement between the plans with 2 and 4 segments per beam. However, the improvement is less important for the plans with 6 segments or more.

Figure 4:
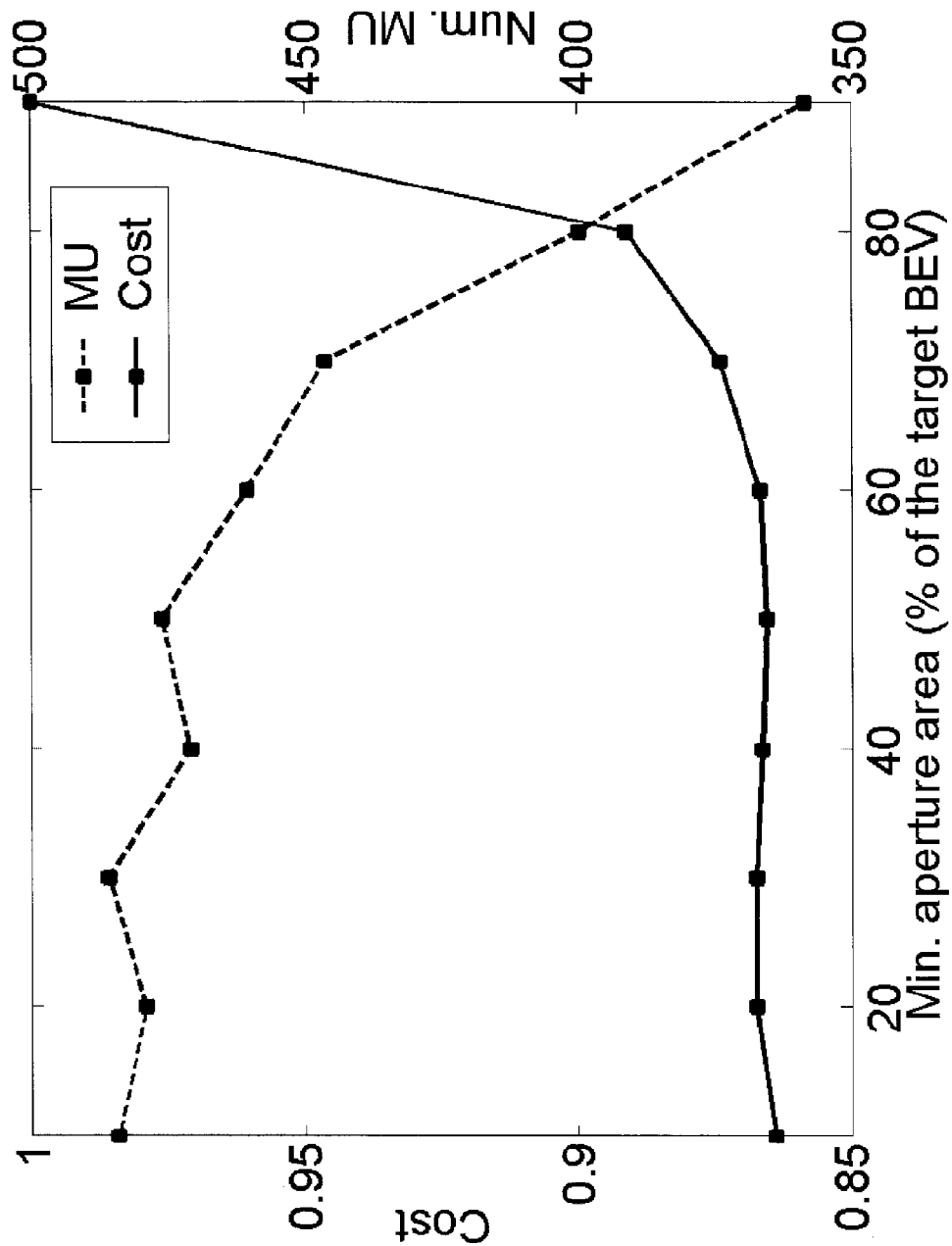
FIG. 4 is a pair of plots showing respectively a value of a cost function and a number of monitor units required by a treatment plan as a function of the value of a constraint on minimum aperture area.

Experiments were done to determine the effect of imposing a constraint on the minimum aperture area for each segment. Nine plans with 6 rotated segments per beam were created by varying the minimum aperture area of each segment. The minimum aperture area was set from 10% to 90% of the beam's eye view (BEV) area of the target. The cost function and the number of monitor units (MU) required for each plan are plotted in FIG. 4.

Figure 5:
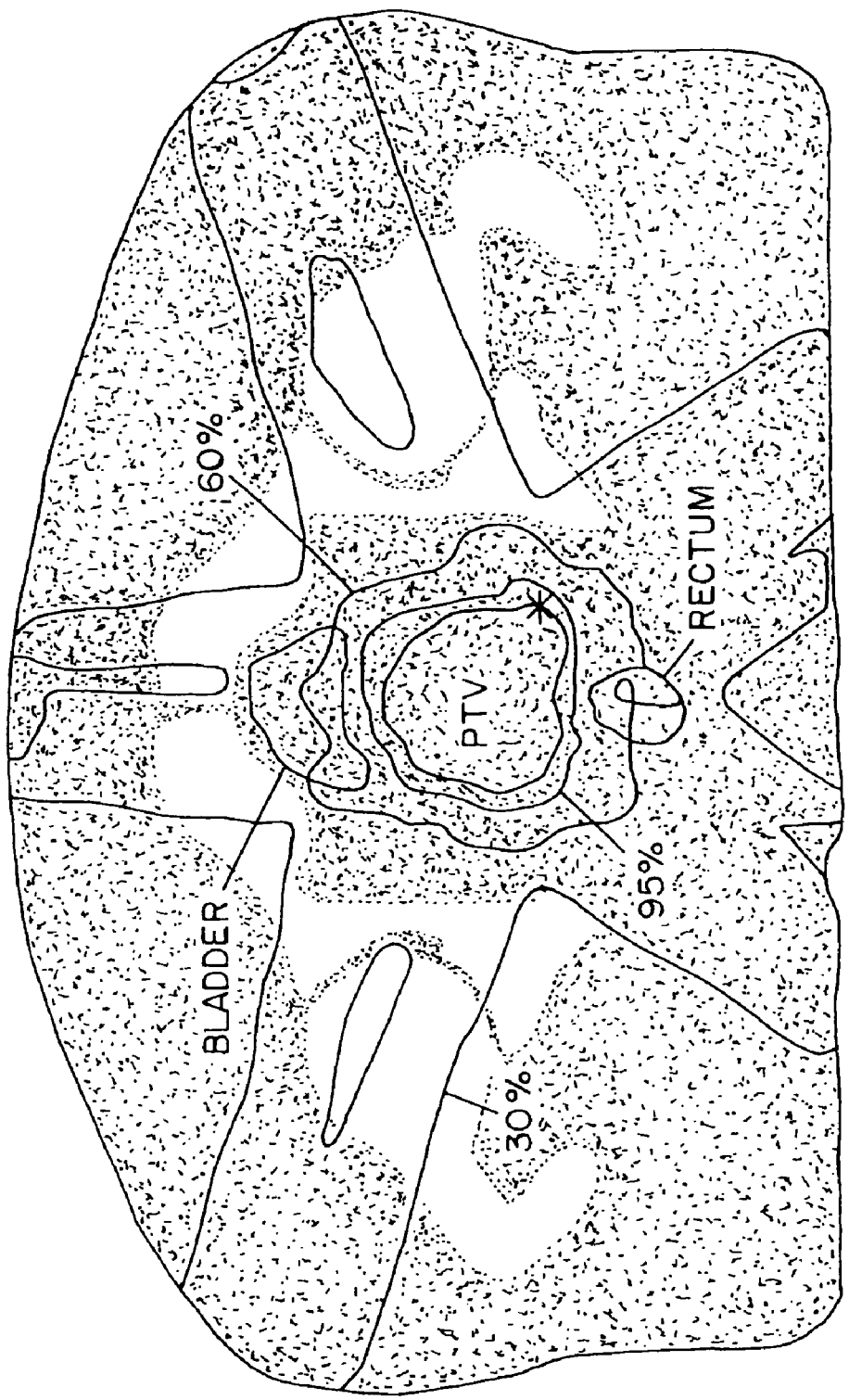
FIG. 5 shows an example optimized dose distribution for a prostate patient.

As the minimum aperture area increases, the cost function increases but the number of MU decreases. When comparing the plans with a minimum aperture area of 10% and 80% of the target BEV, the cost increased by 3% but the number of MU decreased by 20%. The plan with a minimum aperture area of 80% of the BEV (corresponding to 25 $cm^2$) is therefore a good compromise between cost and number of MU. The optimized dose distribution for this plan is shown in FIG. 5. With only 6 segments per beam angle, the 95% isodose encompasses the target, while sparing the rectum and the bladder.

EXAMPLE II

A treatment plan was developed for a patient with recurring nasopharynx carcinoma. The beam energy was 6 MV. A pencil beam (beamlet) size of 2.5 mm by 2.5 mm was used for dose calculations. The voxel size was 2.5 mm by 2.5 mm by 3 mm.

Figure 6:
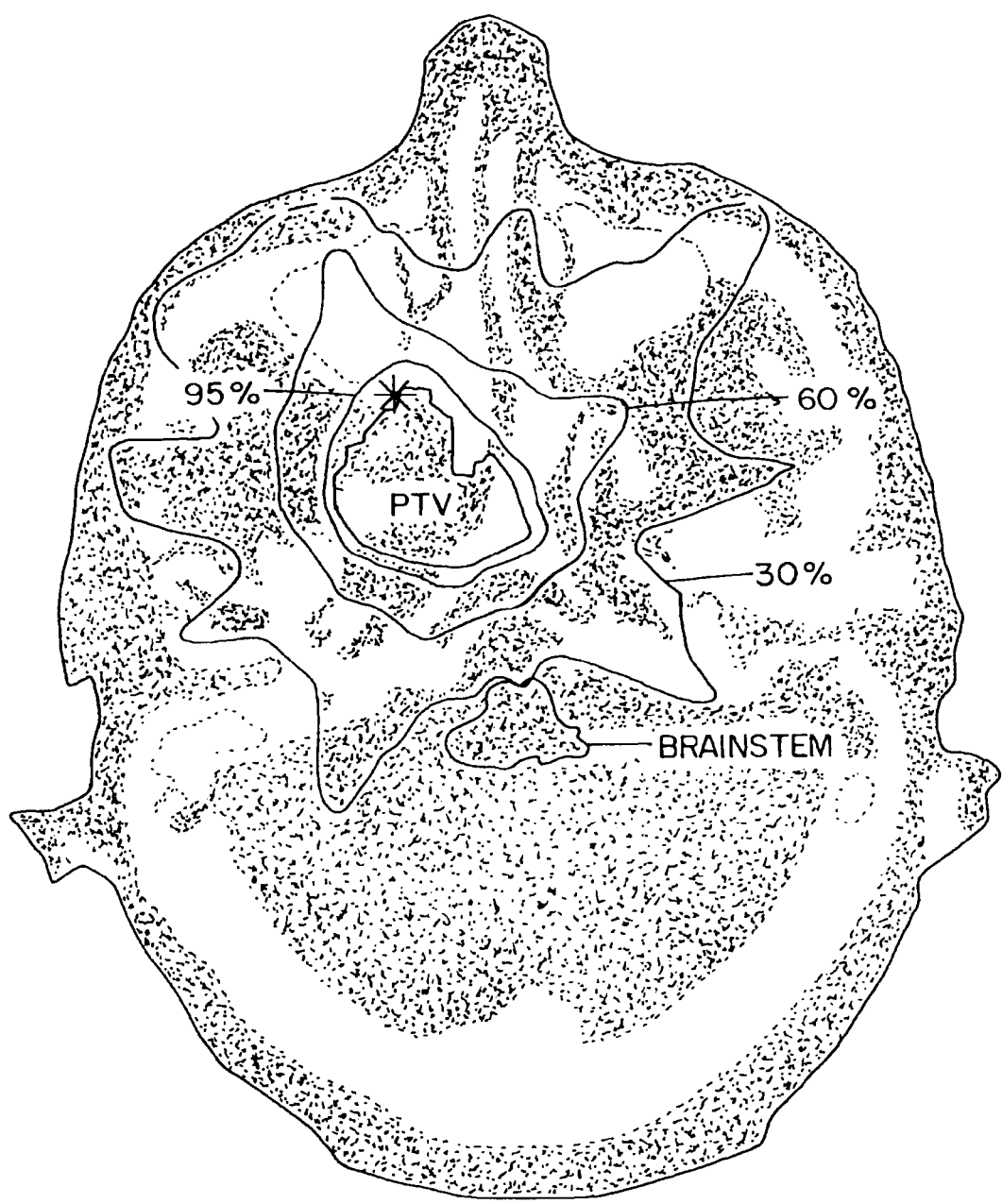
FIG. 6 shows an example optimized dose distribution for a patient exhibiting carcinoma of the nasopharynx.

In this case seven beam angles were used with 6 rotated segments per beam angle. The prescribed dose to the target was 60 Gy. Dose constraints were applied to the brainstem, the left temporal lobe and the right temporal lobe. Due to previous treatment these structures had strongly weighted dose maximum constraints. The right temporal lobe was subdivided into two parts to facilitate the optimization. The first part is a small section of the right temporal lobe located near the target. The second part includes the remainder of the right temporal lobe. The optimized dose distribution for the plan with 6 segments is shown in FIG. 6. The 95% isodose conforms to the PTV and the 30% isodose line is outside the brainstem.

EXAMPLE III

Figure 7A:
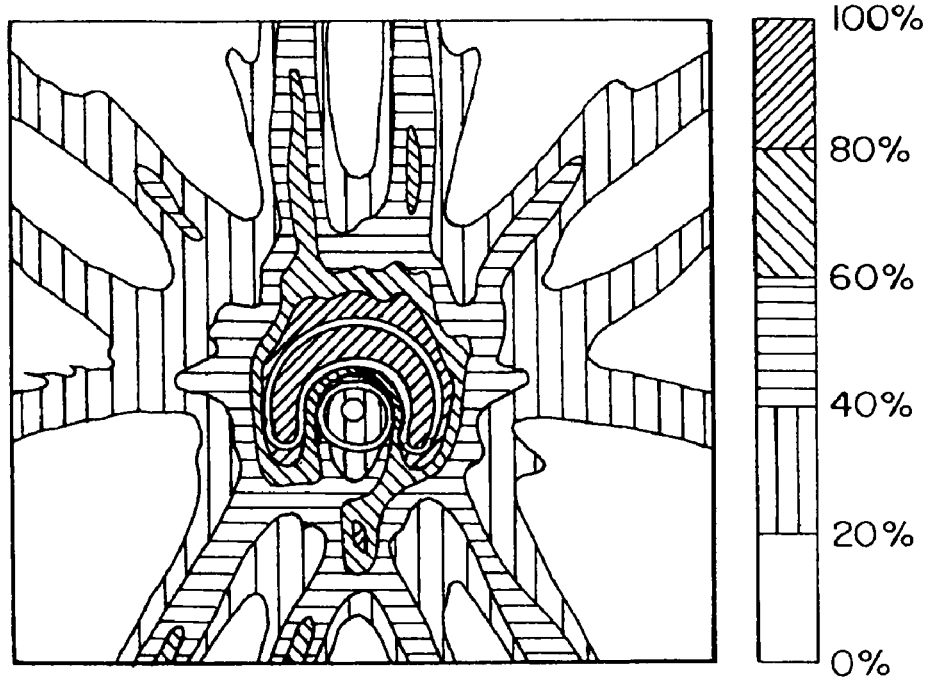
FIGS. 7A and 7B are respectively calculated and measured dose distributions for a C-shaped target.
Figure 7B:
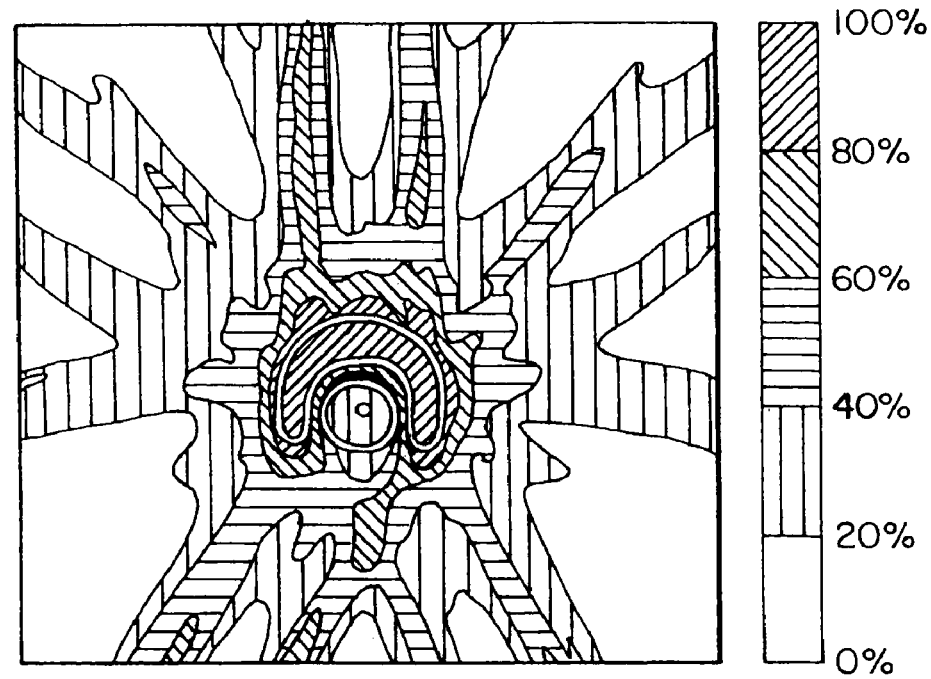

A treatment plan was developed for a complex C-shaped target. Seven equi-spaced beams with six segments per beam were used for the optimization. The prescribed dose to the C-shaped target was 60 Gy. Dose constraints were applied to a centrally located sensitive structure. The optimized plan was delivered with a Varian CL21EX linear accelerator on the AVID™ IMRT phantom (MDX Medical, Vancouver, Canada) to verify the accuracy of the plan. The calculated and measured dose distributions are shown in FIGS. 7A and 7B respectively where the C-shaped target and the critical structure are outlined in white. Although it is not shown on FIGS. 7A or 7B (for clarity), the calculated and measured 95% isodose lines agree within 2.5 mm.

Comparative Examples

For the prostate and nasopharynx patients of Examples I and II, comparison plans were generated using a fluence based dose optimization followed by a collimator rotated leaf sequencing technique, referred to as the rotational leaf motion calculator (RLMC). The same beam arrangement was used in both cases. The Varian CADPLAN HELIOS™ treatment planning system (version 6.27) was first used to optimize the beamlets' intensities. The beamlet size and voxel size were identical to those used in RAO. In a second step, rotated field shapes required to generate the fluence maps were computed with RLMC. RLMC is a leaf sequencing algorithm. RLMC is described in K. Otto and B. G. Clark. Enhancement of IMRT delivery through MLC rotation, Phys. Med. Biol. 47, 3997-4017 (2002). Leaf positions are randomly varied at pre-specified collimator angles with respect to the optimal fluence map generated in the CADPLAN™ treatment planning system.

Figure 8:
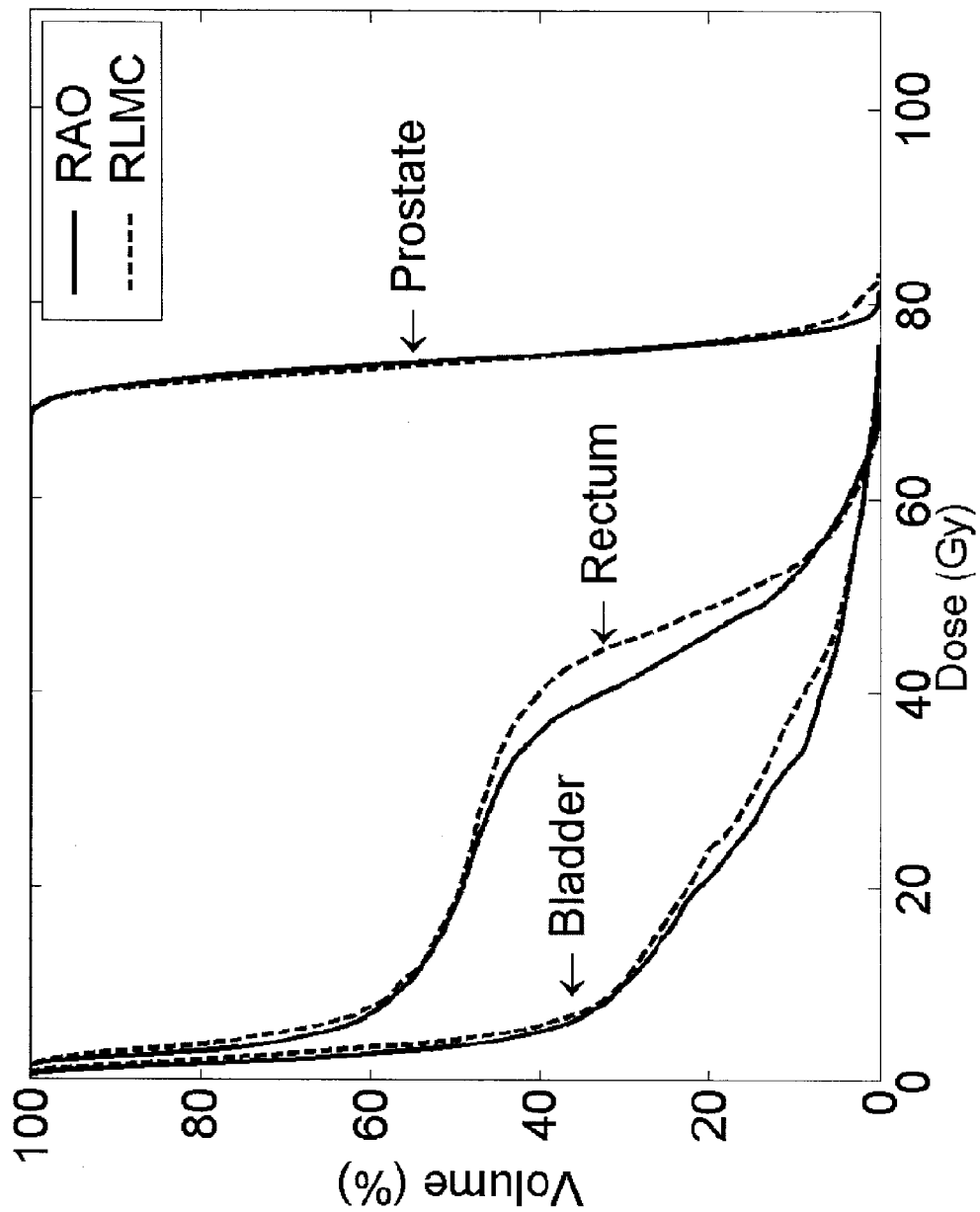
FIG. 8 compares dose-volume histograms for doses that would be delivered to bladder, rectum and prostate of a prostate patient according to an example treatment plan according to this invention and a treatment plan generated according to a prior method.
Figure 9A:
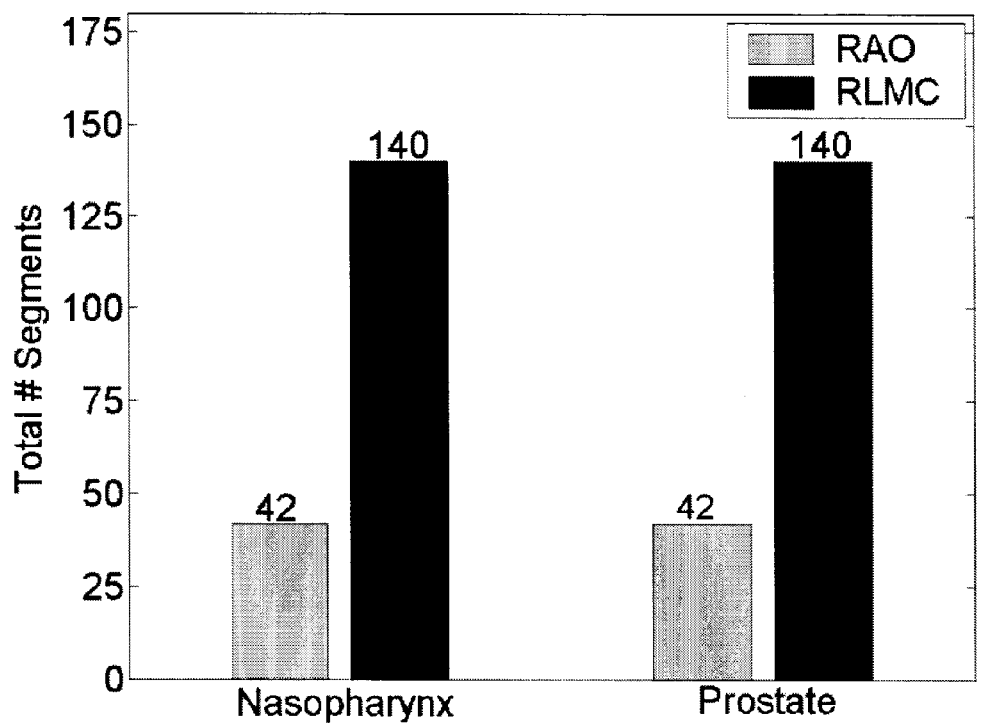
FIGS. 9A and 9B show comparisons of the number of monitor units and the number of segments required for treatment plans according to this invention and treatment plans generated according to prior methods; and, FIGS. 10A and 10B compare dose-volume histograms for doses that would be delivered to various anatomical structures of a patient suffering from carcinoma of the nasopharynx according to an example treatment plan according to this invention and a treatment plan generated according to a prior method.
Figure 9B:
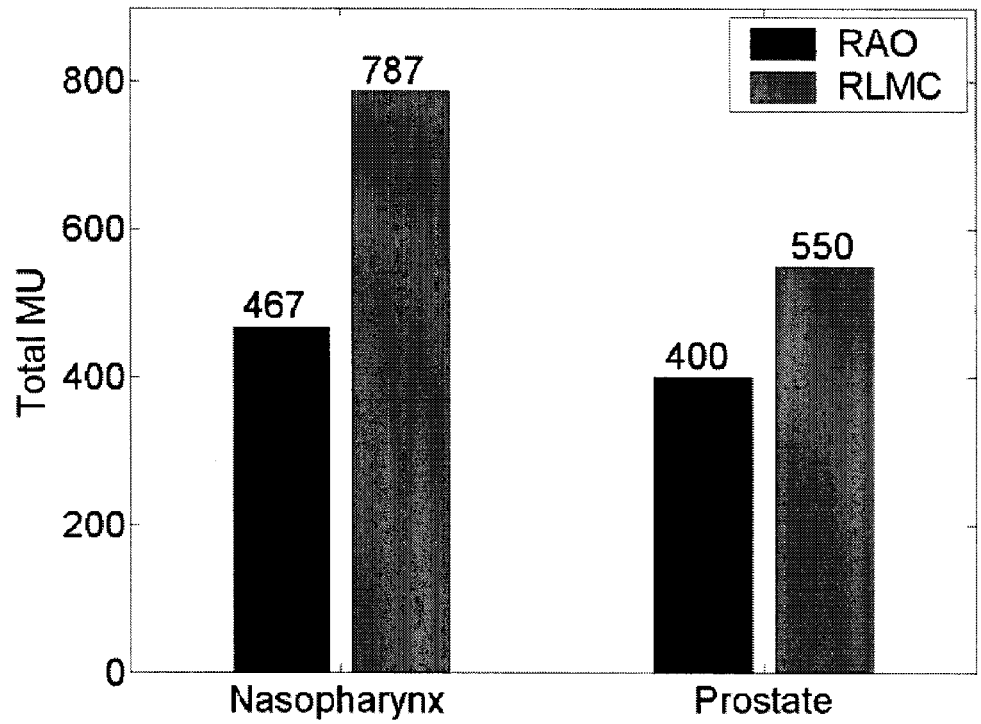

FIG. 8 shows dose volume histograms comparing treatment plans generated according to embodiments of the present invention to treatment plans generated by RLMC for the prostate case of Example I. It is clear that the RAO plan is better than the conventional RLMC plan. The target coverage is slightly better and there is a small improvement in the sparing of the critical structures. FIG. 9 gives a comparison of the number of segments and the number of monitor units required for each plan. The RLMC plan required 550 MU compared to 400 MU for the RAO plan, a 27% reduction.

Figure 10A:
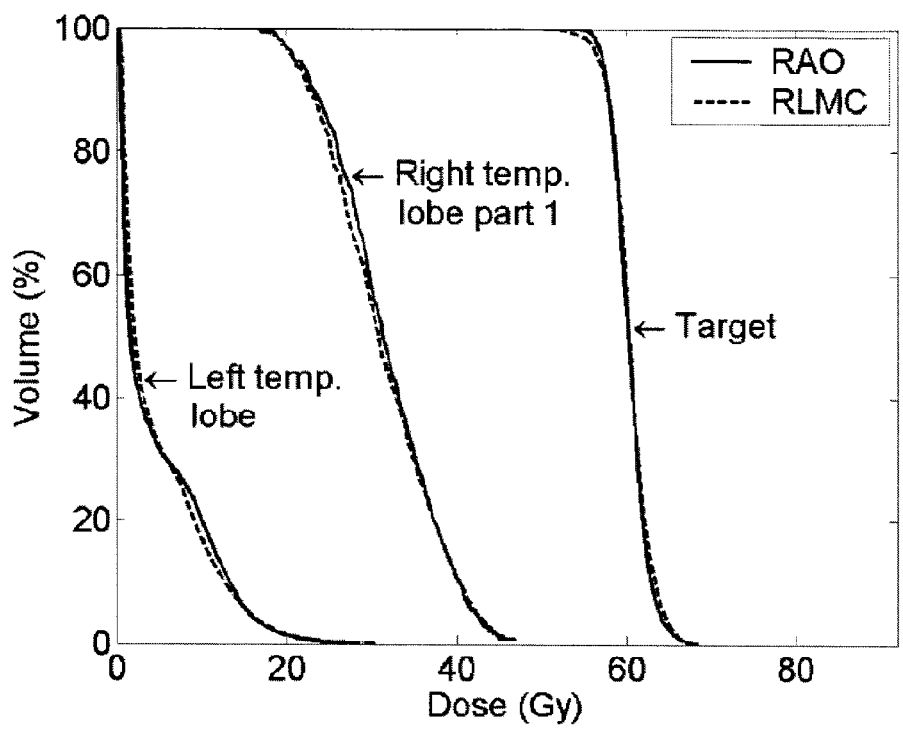
Figure 10B:
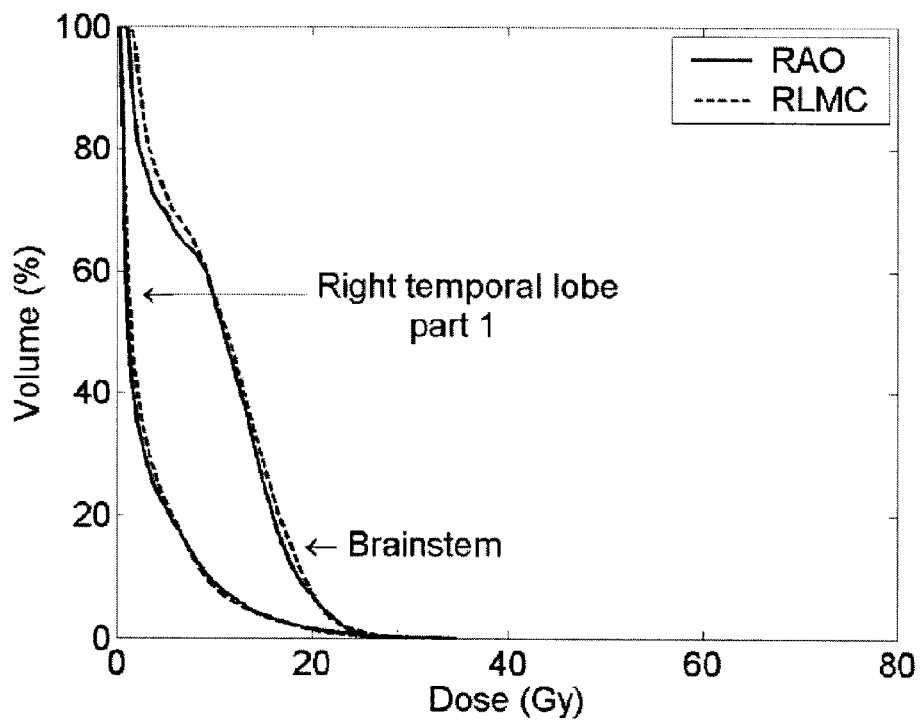

RAO and RLMC plans were also created for the nasopharynx patient of Example II. FIG. 10 compares dose volume histograms for the RAO and RLMC approaches. With the RAO approach, the right temporal lobe part 1 and the brainstem receive slightly less dose while the right temporal lobe part 2 and the left temporal lobe receive slightly more dose. Although it is not obvious which plan is better, similar dosimetric results were obtained for the target and critical structures.

In terms of efficiency, the RAO plan required 6 segments per gantry angle while the RLMC plan required 20 segments per gantry angle. Also, as shown in FIG. 9, the RAO plan required 467 MU to deliver the prescribed dose for one fraction compared to 787 MU for the RLMC plan. This corresponds to a 40% reduction in the number of monitor units.

Certain implementations of the invention comprise computer processors which execute software instructions which cause the processors to perform a method of the invention. For example, one or more data processors may implement the method of FIG. 2 by executing software instructions in a program memory accessible to the data processors. The invention may also be provided in the form of a program product. The program product may comprise any medium which carries a set of computer-readable signals comprising instructions which, when executed by a data processor, cause the data processor to execute a method of the invention. Program products according to the invention may be in any of a wide variety of forms. The program product may comprise, for example: physical media such as magnetic data storage media including floppy diskettes, hard disk drives, optical data storage media including CD ROMs, DVDs, electronic data storage media including ROMs, flash RAM, or the like; or transmission-type media such as digital or analog communication links. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. For example:

The number of segments per beam and/or the collimator rotation angles of the segments may be included as variables in the optimization or may be adjusted manually. Assigning a number of segments to each beam depending upon the complexity of the shape presented by the projection of the target to that beam and selecting collimator rotation angles that permit the collimator to most closely match a desired shape may provide further improvements in dose distribution and/or efficiency.

The methods and apparatus described herein are not limited to delivering IMRT treatments.

In some embodiments, where segments are at closely-spaced angles, radiation may be delivered during rotation of the collimator or gantry.

Accordingly, the scope of the invention is to be construed in accordance with the substance defined by the following claims.

What is claimed is:

1. A method for use in radiation treatment, the method comprising:
    modifying a set of variables to reduce a cost function, the set of variables defining apertures for a plurality of segments including at least first and second segments respectively corresponding to different first and second angles of rotation of a collimator about a beam direction; and
    computing the cost function based at least in part upon a volume dose distribution computed for the set of variables;
    comprising computing the volume dose distribution by, for at least one of the segments, identifying one or more beamlets defined by a fluence grid, wherein the one or more beamlets is partially obstructed by a structure defining the aperture and scaling contributions of the one or more beamlets to the computed volumetric dose distribution by a factor proportional to an area of the beamlet that is unobstructed relative to a total area of the beamlet.

2. A method according to claim 1 comprising looking up the factor in a list of factors that have been predetermined for a plurality of collimator leaf configurations for a plurality of angles of rotation of the collimator.

3. A method according to claim 1 comprising including in the contribution of the partially-obstructed beamlet to the volume dose distribution an amount proportional to an area of the beamlet that is obstructed relative to a total area of the beamlet and to a fraction of incident radiation transmitted through a part of the collimator that is partially obstructing the beamlet.

4. A method for use in radiation treatment, the method comprising:
    modifying a set of variables to reduce a cost function, the set of variables defining apertures for a plurality of segments including at least first and second segments respectively corresponding to different first and second angles of rotation of a collimator about a beam direction; and
    computing the cost function based at least in part upon a volume dose distribution computed for the set of variables;
    wherein the collimator comprises a multi-leaf collimator comprising a plurality of leaves and the method comprises computing the volume dose distribution by providing a fluence grid defining an array of beamlets arranged along grid lines and, based at least in part upon the fluence grid, determining a contribution to the volume dose distribution by one or more of the segments that corresponds to an angle of rotation of the collimator for which the leaves of the multi-leaf collimator are not aligned with the grid lines of the fluence grid.

5. A method according to claim 4 wherein modifying the set of variables comprises modifying one or more variables of the set of variables subject to an area constraint on a minimum area of at least one of the apertures.

6. A method according to claim 5 wherein the area constraint requires the aperture defined for each of the plurality of segments to have an area that is at least a specified proportion of a projected area of a target in a beam direction corresponding to the segment.

7. A method according to claim 6 wherein the specified proportion is at least 40%.

8. A method according to claim 7 wherein the specified proportion is 60% or more.

9. A method according to claim 4 wherein each of the apertures shapes one of a plurality of beams, the variables include weights for the beams and each of the beams has a weight of zero or more.

10. A method according to claim 9 where the plurality of beams includes at least 3 beams.

11. A method according to claim 4 comprising initializing the set of variables so that, for a plurality of the segments, the apertures approximate a projection of a target in a beam direction corresponding to the segment.

12. A method according to claim 4 wherein computing the cost function comprises computing differences between the volume dose distribution and a prescribed volume dose distribution.

13. A method according to claim 4 further comprising, when the set of variables satisfies a termination criterion, programming a radiation delivery device to deliver radiation to a subject according to the set of variables.

14. A method according to claim 4 wherein the variables include collimator rotation angles corresponding to one or more of the segments.

15. A method according to claim 4 wherein the set of variables includes values for the angles of rotation of the collimator and wherein optimizing the set of variables comprises changing at least one of the values for the angles of rotation of the collimator.

16. A method for use in radiation treatment, the method comprising:
    modifying a set of variables to reduce a cost function, the set of variables defining apertures for a plurality of segments including at least first and second segments respectively corresponding to different first and second angles of rotation of a collimator about a beam direction; and computing the cost function based at least in part upon a volume dose distribution computed for the set of variables wherein each of the apertures shapes one of a plurality of beams, each beam comprising one or more pencil beams, and wherein at least one of the pencil beams is partially obstructed by a structure defining one of the apertures, wherein the method comprises determining a contribution of the partially-obstructed pencil beam to the volume dose distribution by a process comprising scaling the contribution of the partially-obstructed pencil beam in proportion to an area of the pencil beam that is unobstructed relative to a total area of the pencil beam.

17. A method according to claim 16 wherein the plurality of segments includes segments corresponding to two or more beam angles.

18. A method according to claim 17 wherein, for each of the beam angles, the plurality of segments includes segments corresponding to a plurality of angles of rotation of the collimator.

19. A method according to claim 17 wherein each of the beams has a weight of zero or more.

20. A method according to claim 16 comprising including in the contribution of the partially-obstructed pencil beam to the volume dose distribution an amount proportional to an area of the pencil beam that is obstructed relative to a total area of the pencil beam and to a fraction of incident radiation transmitted through a part of the collimator that is partially obstructing the pencil beam.

21. A method according to claim 16 wherein modifying the variables comprises applying a simulated annealing algorithm to the set of variables.

22. A method according to claim 16 wherein modifying the set of variables comprises modifying one or more variables of the set of variables subject to an area constraint on a minimum area of at least one of the apertures.

23. A method according to claim 22 wherein the area constraint requires the aperture defined for each of the segments to have an area that is at least a specified proportion of a projected area of a target in a beam direction corresponding to the segment.

24. A method according to claim 23 wherein the specified fraction is at least 40%.

25. A method according to claim 23 wherein the specified fraction is 60% or more.

26. A method according to claim 16 wherein the variables include weights for the beams and each of the beams has a weight of zero or more.

27. A method according to claim 16 where the plurality of beams includes at least 3 beams.

28. A method according to claim 16 comprising initializing the set of variables so that, for a plurality of the segments, the apertures approximate a projection of a target in a beam direction corresponding to the segment.

29. A method according to claim 16 wherein computing the cost function comprises computing differences between the volume dose distribution and a prescribed volume dose distribution.

30. A method according to claim 16 further comprising, when the set of variables satisfies a termination criterion, programming a radiation delivery device to deliver radiation to a subject according to the set of variables.

31. A method according to claim 16 wherein the variables include collimator rotation angles corresponding to one or more of the segments.

32. A method according to claim 16 wherein the set of variables includes values for the angles of rotation of the collimator and wherein optimizing the set of variables comprises changing at least one of the values for the angles of rotation of the collimator.

33. A method for use in radiation treatment of a target in a subject, the method comprising:
providing a prescribed volume dose distribution;
initializing a set of variables, the set of variables including collimator configurations for a plurality of segments, the segments corresponding to a plurality of angles of rotation of a rotatable multi-leaf collimator and a plurality of beams, each of the collimator configurations specifying positions of leaves of the collimator;
determining a computed volume dose distribution for the set of variables;
computing a cost function based at least in part on differences between the computed volume dose distribution and the prescribed volume dose distribution and making the cost function a current cost function; and,
optimizing the set of variables by, until a termination condition is satisfied:
changing one or more variables of the set of variables to yield a changed set of variables;
computing an updated cost function for the changed set of variables; and,
based at least in part upon a comparison of the updated cost function to the current cost function, determining whether or not to make the changed set of variables the current set of variables and the updated cost function the current cost function;
wherein determining the computed volume dose distribution comprises, for at least one of the segments, identifying one or more beamlets defined by a fluence grid wherein the one or more beamlets is partially obstructed by the collimator and scaling contributions of the one or more beamlets to the computed volume dose distribution in proportion to an area of the beamlet that is unobstructed by the multi-leaf collimator relative to a total area of the beamlet.

34. A method according to claim 33 comprising including in the contribution of the partially-obstructed beamlet to the volume dose distribution an amount proportional to an area of the beamlet that is obstructed relative to a total area of the beamlet and to a fraction of incident radiation transmitted through a part of the collimator that is partially obstructing the beamlet.

35. A method for use in radiation treatment of a target in a subject, the method comprising:
providing a prescribed volume dose distribution;
initializing a set of variables, the set of variables including collimator configurations for a plurality of segments, the segments corresponding to a plurality of angles of rotation of a rotatable multi-leaf collimator and a plurality of beams, each of the collimator configurations specifying positions of leaves of the collimator;
determining a computed volume dose distribution for the set of variables;
computing a cost function based at least in part on differences between the computed volume dose distribution and the prescribed volume dose distribution and making the cost function a current cost function; and,
optimizing the set of variables by, until a termination condition is satisfied:
changing one or more variables of the set of variables to yield a changed set of variables;
computing an undated cost function for the changed set of variables; and, based at least in part upon a comparison of the updated cost function to the current cost function, determining whether or not to make the changed set of variables the current set of variables and the updated cost function the current cost function wherein determining the computed volume dose distribution comprises providing a fluence grid defining an array of beamlets and, based at least in part upon the fluence grid, determining a contribution to the computed volume dose distribution by one or more of the segments corresponding to an angle of rotation of the collimator for which the leaves of the multi-leaf collimator are not aligned with grid lines of the fluence grid.

36. A method for use in radiation treatment of a target in a subject, the method comprising:

providing a prescribed volume dose distribution;

initializing a set of variables, the set of variables including collimator configurations for a plurality of segments, the segments corresponding to a plurality of angles of rotation of a rotatable multi-leaf collimator and a plurality of beams, each of the collimator configurations specifying positions of leaves of the collimator;

determining a computed volume dose distribution for the set of variables;

computing a cost function based at least in part on differences between the computed volume dose distribution and the prescribed volume dose distribution and making the cost function a current cost function; and, optimizing the set of variables by, until a termination condition is satisfied:

changing one or more variables of the set of variables to yield a changed set of variables;

computing an updated cost function for the changed set of variables; and based at least in part upon a comparison of the updated cost function to the current cost function, determining whether or not to make the changed set of variables the current set of variables and the updated cost function the current cost function wherein each beam comprises one or more pencil beams, and wherein at least one of said pencil beams is partially obstructed by the multileaf collimator, wherein the method comprises scaling a contribution to the calculated dose from said partially obstructed pencil beam in proportion to an area of the pencil beam that is unobstructed relative to a total area of the pencil beam.

37. Radiation treatment apparatus for controlling a radiation delivery machine comprising a collimator, the apparatus comprising:

dose computation means for computing a volume dose distribution corresponding to a set of variables defining apertures for a plurality of segments including at least first and second segments respectively corresponding to different first and second angles of rotation of the collimator about a beam direction;

means for evaluating a value of a cost function based at least in part upon a volume dose distribution from the dose computation means the volume dose distribution computed for the set of variables; and, means for modifying the set of variables to reduce the value of the cost function;

wherein the collimator comprises a multi-leaf collimator comprising a plurality of leaves and the dose computation means is operable to compute the volume dose distribution by providing a fluence grid defining an array of beamlets arranged along grid lines and, based at least in part upon the fluence grid, determining a contribution to the volume dose distribution by one or more of the segments that corresponds to an angle of rotation of the collimator for which the leaves of the multileaf collimator are not aligned with the grid lines of the fluence grid.

38. Radiation treatment planning apparatus comprising a data processor configured to perform a method comprising:

modifying a set of variables to reduce a cost function, the set of variables defining apertures for a plurality of segments including at least first and second segments respectively corresponding to different first and second angles of rotation of a collimator about a beam direction; and computing the cost function based at least in part upon a volume dose distribution computed for the set of variables;

wherein the collimator comprises a multileaf collimator comprising a plurality of leaves and the method comprises computing the volume dose distribution by providing a fluence grid defining an array of beamlets arranged along grid lines and, based at least in part upon the fluence grid, determining a contribution to the volume dose distribution by one or more of the segments that corresponds to an angle of rotation of the collimator for which the leaves of the multi-leaf collimator are not aligned with the grid lines of the fluence grid.

39. Radiation treatment planning apparatus comprising a data processor configured to perform a method comprising:

modifying a set of variables to reduce a cost function, the set of variables defining apertures for a plurality of segments including at least first and second segments respectively corresponding to different first and second angles of rotation of a collimator about a beam direction; and computing the cost function based at least in part upon a volume dose distribution computed for the set of variables wherein each of the apertures shapes one of a plurality of beams, each beam comprising one or more pencil beams, and wherein at least one of the pencil beams is partially obstructed by a structure defining one of the apertures, wherein the method comprises determining a contribution of the partially-obstructed pencil beam to the volume dose distribution by a process comprising scaling the contribution of the partially-obstructed pencil beam in proportion to an area of the pencil beam that is unobstructed relative to a total area of the pencil beam.

* * * * *